(12) United States Patent
Kothandaraman (10) Patent No.: US 9,623,244 B2
(45) Date of Patent: Apr. 18, 2017

(54) NEUROMODULATION SYSTEM AND METHOD FOR AUTOMATICALLY ADJUSTING STIMULATION PARAMETERS TO OPTIMIZE POWER CONSUMPTION

(71) Applicant: BOSTON SCIENTIFIC NEUROMODULATION CORPORATION, Valencia, CA (US)

(72) Inventor: Sridhar Kothandaraman, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 183 days.

(21) Appl. No.: 14/186,995

(22) Filed: Feb. 21, 2014

(65) Prior Publication Data

US 2014/0243925 A1    Aug. 28, 2014

Related U.S. Application Data

(60) Provisional application No. 61/768,319, filed on Feb. 22, 2013.

(51) Int. Cl.
    *A61N 1/36*    (2006.01)
(52) U.S. Cl.
    CPC ..... *A61N 1/36071* (2013.01); *A61N 1/36146* (2013.01)
(58) Field of Classification Search
    CPC .................. A61N 1/36071; A61N 1/36146
    See application file for complete search history.

(56) References Cited

U.S. PATENT DOCUMENTS 6,895,280 B2    5/2005  Meadows et al.
2007/0142874 A1*  6/2007  John .................... A61N 1/3605
                                                607/45
(Continued)

FOREIGN PATENT DOCUMENTS

CN    101939044 A    1/2011
CN    105142718 A    12/2015
(Continued)

OTHER PUBLICATIONS

"International Application Serial No. PCT/US2014/017812, International Preliminary Report on Patentability mailed Sep. 3, 2015", 8 pgs.

(Continued)

*Primary Examiner* — Rex R Holmes
(74) *Attorney, Agent, or Firm* — Schwegman Lundberg & Woessner, P.A.

(57) ABSTRACT

An electrical neuromodulation system configured for minimizing energy consumption of a neuromodulation device includes an external control device configured for receiving input from a user, the neuromodulation device in communication with the external control device, and control/processing circuitry. The control/processing circuitry is configured for automatically (a) adjusting a modulation parameter value (e.g., by a step size) to create a currently adjusted modulation parameter value that decreases the energy consumption of the neuromodulation device, (b) instructing the neuromodulation device to deliver electrical energy to at least one electrode in accordance with the currently adjusted modulation parameter value, (c) determining whether a manual parameter adjustment was made by the user in response to step (b), and (d) if the manual parameter adjustment was not made, deeming the currently adjusted (Continued)

modulation parameter value as a previously adjusted modulation parameter value and repeating steps (a)-(d).

34 Claims, 6 Drawing Sheets (56) References Cited

U.S. PATENT DOCUMENTS

| | | | |
|---|---|---|---|
| 2008/0288023 A1* | 11/2008 | John | A61N 1/37247 607/59 |
| 2009/0118786 A1 | 5/2009 | Meadows et al. | |
| 2011/0106213 A1 | 5/2011 | Davis et al. | |
| 2014/0005744 A1* | 1/2014 | Hershey et al. | 607/46 |

FOREIGN PATENT DOCUMENTS

| | | |
|---|---|---|
| JP | 2016507336 A | 3/2016 |
| WO | WO-2007097861 A1 | 8/2007 |
| WO | WO-2008052085 A1 | 5/2008 |
| WO | WO-2014130881 | 8/2014 |

OTHER PUBLICATIONS

"International Application Serial No. PCT/US2014/017812, International Search Report mailed Jun. 6, 2014", 4 pgs.

* cited by examiner

NEUROMODULATION SYSTEM AND METHOD FOR AUTOMATICALLY ADJUSTING STIMULATION PARAMETERS TO OPTIMIZE POWER CONSUMPTION

RELATED APPLICATION DATA

The present application claims the benefit under 35 U.S.C. §119 to U.S. provisional patent application Ser. No. 61/768,319, filed Feb. 22, 2013. The foregoing application is hereby incorporated by reference into the present application in its entirety.

FIELD OF THE INVENTION

The present inventions relate to tissue modulation systems, and more particularly, to systems and methods for adjusting the modulation provided to tissue to minimize the energy requirements of the systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of spinal modulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neuromodulation systems typically includes one or more electrode carrying modulation leads, which are implanted at the desired stimulation site, and a neuromodulation device implanted remotely from the stimulation site, but coupled either directly to the modulation lead(s) or indirectly to the modulation lead(s) via a lead extension. Thus, electrical pulses can be delivered from the neuromodulation device to the electrode(s) to activate a volume of tissue in accordance with a set of modulation parameters and provide the desired efficacious therapy to the patient. In particular, electrical energy conveyed between at least one cathodic electrode and at least one anodic electrode creates an electrical field, which when strong enough, depolarizes (or "stimulates") the neurons beyond a threshold level, thereby inducing the firing of action potentials (APs) that propagate along the neural fibers. A typical modulation parameter set may include the electrodes that are sourcing (anodes) or returning (cathodes) the modulating current at any given time, as well as the amplitude, duration, and rate of the stimulation pulses.

The neuromodulation system may further comprise a handheld patient programmer to remotely instruct the neuromodulation device to generate electrical stimulation pulses in accordance with selected modulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

Of course, neuromodulation devices are active devices requiring energy for operation, and thus, the neuromodulation system may oftentimes include an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be used to directly power the electronic componentry contained within the neuromodulation device, or can be stored in a rechargeable battery within the neuromodulation device, which can then be used to power the electronic componentry on-demand.

Typically, the therapeutic effect for any given neuromodulation application may be optimized by adjusting the modulation parameters. Often, these therapeutic effects are correlated to the diameter of the nerve fibers that innervate the volume of tissue to be modulated. For example, in SCS, activation (i.e., recruitment) of large diameter sensory fibers is believed to reduce/block transmission of smaller diameter pain fibers via interneuronal interaction in the dorsal horn of the spinal cord. Activation of large sensory fibers also typically creates a sensation known as paresthesia that can be characterized as an alternative sensation that replaces the pain signals sensed by the patient.

Although alternative or artifactual sensations are usually tolerated relative to the sensation of pain, patients sometimes report these sensations to be uncomfortable, and therefore, they can be considered an adverse side-effect to neuromodulation therapy in some cases. It has been shown that high-frequency pulsed electrical energy can be effective in providing neuromodulation therapy for chronic pain without causing paresthesia. In contrast to conventional neuromodulation therapies, which employ low- to mid-frequencies to provide a one-to-one correspondence between the generation of an AP and each electrical pulse, high frequency modulation (e.g., 1 KHz-50 KHz) can be employed to block naturally occurring APs within neural fibers or otherwise disrupt the APs within the neural fibers. Although high-frequency modulation therapies have shown good efficacy in early studies, one notable drawback is the relatively high energy requirement to achieve high-frequency modulation in contrast to low- to mid-frequency modulation. In particular, the amount of energy required to generate an electrical waveform is proportional to the frequency of the electrical waveform. Thus, neuromodulation devices that generate relatively low frequency modulation energy typically need to be recharged only once every 1-2 weeks, whereas neuromodulation devices that generate relatively high frequency modulation energy may require a daily or more frequent recharge.

There, thus, remains a need to decrease the energy requirements for high-frequency neuromodulation therapy.

SUMMARY OF THE INVENTION

In accordance with a first aspect of the present inventions, an electrical neuromodulation system is provided. The system includes an external control device configured for receiving input from a user, and a neuromodulation device in communication with the external control device, and configured for delivering electrical energy to at least one electrode in accordance with a modulation parameter value. The neuromodulation device may be configured for conveying the electrical energy at any frequency. However, the present invention lends itself well to frequencies in the range of 1200 Hz-50 KHz where energy consumption is a more critical consideration. The system may further include memory configured for storing the modulation parameter value, and/or a battery configured for storing power used to generate the electrical energy.

The system also includes control/processing circuitry, which may be contained in the neuromodulation device, or in the external control device. The control/processing circuitry is configured for automatically (a) adjusting the modulation parameter value (e.g., by a step size) to create a currently adjusted modulation parameter value that decreases the energy consumption of the neuromodulation device, and (b) instructing the neuromodulation device to deliver the electrical energy to the at least one electrode in accordance with the currently adjusted modulation parameter value. The electrical energy may be pulsed electrical energy. The modulation parameter value may be a pulse rate value, a pulse width value, a duty cycle value, an amplitude value, and/or an electrode combination value.

The control/processing circuitry is further configured for (c) determining whether a manual parameter adjustment was made by the user in response to step (b). The manual parameter adjustment made by the user may include a manual adjustment of pulse rate, pulse width, duty cycle, amplitude, and/or electrode combination.

The control/processing circuitry is further configured for (d) if the manual parameter adjustment was not made, deeming the currently adjusted modulation parameter value as a previously adjusted modulation parameter value and repeating steps (a)-(d). The control/processing circuitry may be configured for repeating steps (a)-(d) only if the manual parameter adjustment is not made within a predetermined time period after step (b) is initiated. The control/processing circuitry may be further configured for, if the manual parameter adjustment is made, determining that the previously adjusted modulation parameter value is an optimized modulation parameter value that minimizes energy consumption of the neuromodulation device. Still further, the control/processing circuitry may be configured for, if the manual parameter adjustment is made, automatically instructing the neuromodulation device to again deliver the electrical energy to the at least one electrode in accordance with the previously adjusted modulation parameter value.

The modulation parameter value may be a first modulation parameter value, and the control/processing circuitry may be further configured for (e) adjusting a second modulation parameter value to create a currently adjusted second modulation parameter value that decreases the energy consumption of the neuromodulation device, (f) instructing the neuromodulation device to deliver the electrical energy to the at least one electrode in accordance with the currently adjusted second modulation parameter value, (g) determining whether a manual parameter adjustment was made by the user in response to step (f), and (h) if the manual parameter adjustment was not made, deeming the currently adjusted second modulation parameter value as a previously adjusted second modulation parameter value, and repeating steps (e)-(h).

In accordance with a second aspect of the present inventions, a method of minimizing energy consumption of a neuromodulation device is provided. The method includes: (a) adjusting a modulation parameter value (e.g., by a step size) to create a currently adjusted modulation parameter value that decreases the energy consumption of the neuromodulation device; and (b) delivering electrical energy from the neuromodulation device to at least one electrode adjacent a target tissue site in accordance with the currently adjusted modulation parameter value, thereby modulating (e.g., stimulating) the target tissue site. The at least one electrode may be implanted within the patient. In one embodiment, the electrical energy is delivered from the neuromodulation device at a frequency in the range of 1200 Hz-50 KHz, although lower frequencies are possible. The electrical energy may be pulsed electrical energy. The modulation parameter value may be a pulse rate value, a pulse width value, a duty cycle value, an amplitude value, and/or an electrode combination value.

The method further includes (c) determining whether a manual parameter adjustment was made by a user in response to step (b). The manual parameter adjustment may include an adjustment to pulse rate, pulse width, duty cycle, amplitude, and/or electrode combination.

The method further includes (d) if the manual parameter adjustment is not made, deeming the currently adjusted modulation parameter value as a previously adjusted modulation parameter value, and repeating steps (a)-(d). In one embodiment, steps (a)-(d) are repeated only if the manual parameter adjustment is not made within a predetermined time period after step (b) is initiated. The method may further include, if the manual parameter adjustment is made, determining that the previously adjusted modulation parameter value is an optimized modulation parameter value that minimizes energy consumption of the neuromodulation device when delivering the electrical energy to the at least one electrode. Still further, the method may include, if the manual parameter adjustment is made, again delivering the electrical energy to the at least one electrode in accordance with the previously adjusted modulation parameter value.

The modulation parameter value may be a first modulation parameter value, and the method may further include: (e) adjusting a second modulation parameter value to create a currently adjusted second modulation parameter value that decreases the energy consumption of the neuromodulation device; (f) delivering the electrical energy from the neuromodulation device to the at least one electrode adjacent the target tissue site in accordance with the currently adjusted second modulation parameter value, thereby modulating the target tissue site; (g) determining whether the manual parameter adjustment was made by a user in response to step (f); and (h) if the manual parameter adjustment was not made, deeming the currently adjusted second modulation parameter value as a previously adjusted second modulation parameter value, and repeating steps (e)-(h).

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a spinal column modulation (SCM) system. However, it is to be understood that the while the invention lends itself well to applications in SCM, the invention, in its broadest aspects, may not be so limited. Rather, the invention may be used with any type of implantable electrical circuitry used to modulate tissue. For example, the present invention may be used as part of a pacemaker, a defibrillator, a cochlear modulator device, a retinal modulator device, a modulator device configured to produce coordinated limb movement, a cortical modulator device, a deep brain modulator device, peripheral nerve modulator device, micromodulator device, or in any other tissue modulator device configured to treat urinary incontinence, sleep apnea, shoulder sublaxation, headache, etc.

Figure 1:
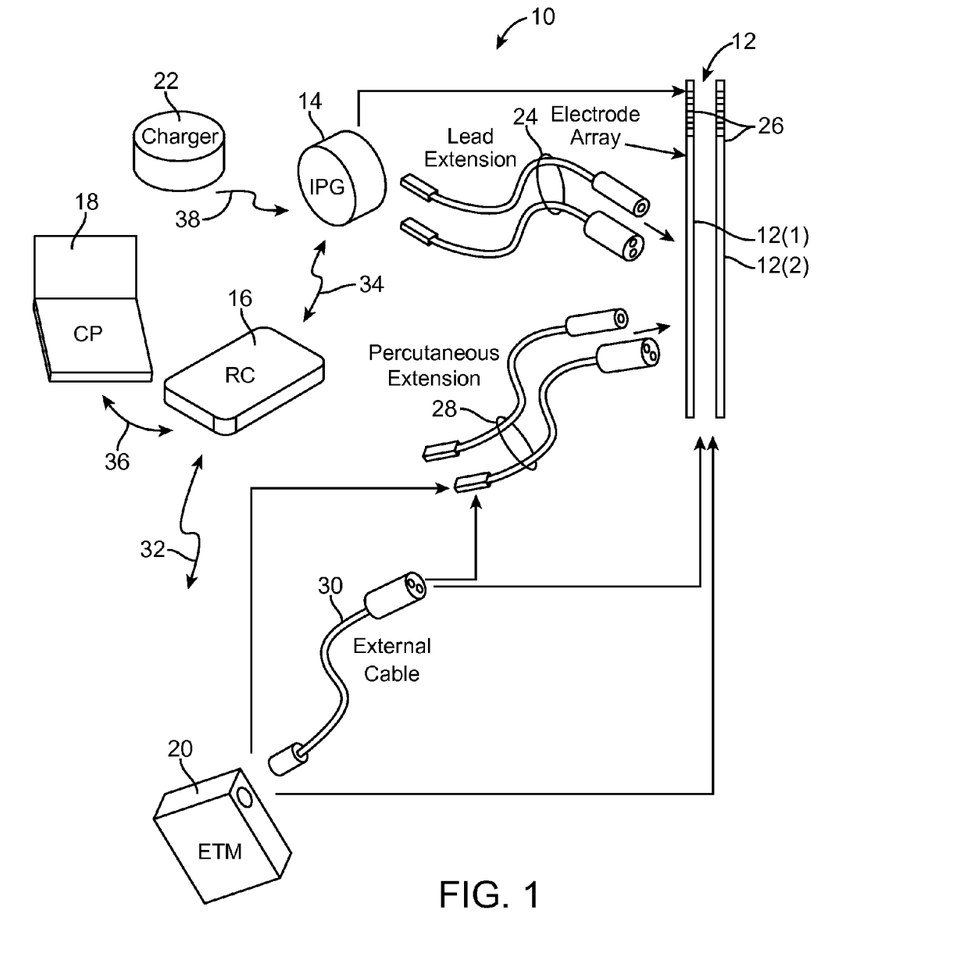
FIG. 1 is plan view of one embodiment of a spinal column modulation (SCM) system arranged in accordance with the present inventions.

Turning first to FIG. 1, an exemplary SCM system 10 generally includes one or more (in this case, two) implantable modulation leads 12(1) and 12(2), a fully implantable modulator (IPG) 14, an external remote controller (RC) 16, a clinician's programmer (CP) 18, an External Trial Modulator (ETM) 20, and an external charger 22.

The IPG 14 is physically connected via one or more percutaneous lead extensions 24 to the modulation leads 12, which carry a plurality of electrodes 26 arranged in an array. In the illustrated embodiment, the modulation leads 12 are percutaneous leads, and to this end, the electrodes 26 are arranged in-line along the modulation leads 12. In alternative embodiments, the electrodes 26 may be arranged in a two-dimensional pattern on a single paddle lead. As will be described in further detail below, the IPG 14 includes pulse generation circuitry that delivers the electrical modulation energy in the form of an electrical pulse train to the electrode array 26 in accordance with a set of modulation parameters.

The ETM 20 may also be physically connected via percutaneous lead extensions 28 and an external cable 30 to the modulation leads 12. The ETM 20, which has pulse generation circuitry similar to that of the IPG 14, also delivers electrical modulation energy in the form of an electrical pulse train to the electrode array 26. The major difference between the ETM 20 and the IPG 14 is that the ETM 20 is a non-implantable device that is used on a trial basis after the modulation leads 12 have been implanted and prior to implantation of the IPG 14, to test the responsiveness of the modulation that is to be provided. Thus, any functions described herein with respect to the IPG 14 can likewise be performed with respect to the ETM 20. Further details of an exemplary ETM are described in U.S. Pat. No. 6,895,280, which is expressly incorporated herein by reference.

The RC 16 may be used to telemetrically control the ETM 20 via a bi-directional RF communications link 32. Once the IPG 14 and modulation leads 12 are implanted, the RC 16 may be used to telemetrically control the IPG 14 via a bi-directional RF communications link 34. Such control allows the IPG 14 to be turned on or off and to be programmed with different modulation parameter sets. The RC 16 may also be operated to modify the programmed modulation parameters to actively control the characteristics of the electrical modulation energy output by the IPG 14.

The CP 18 provides clinician detailed modulation parameters for programming the IPG 14 and ETM 20 in the operating room and in follow-up sessions. The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown).

The external charger 22 is a portable device used to transcutaneously charge the IPG 14 via an inductive link 38. For purposes of brevity, the details of the external charger 22 will not be described herein. Details of exemplary embodiments of external chargers are disclosed in U.S. Pat. No. 6,895,280, which has been previously incorporated herein by reference. Once the IPG 14 has been programmed, and its power source has been charged by the external charger 22 or otherwise replenished, the IPG 14 may function as programmed without the RC 16 or CP 18 being present.

Figure 2:
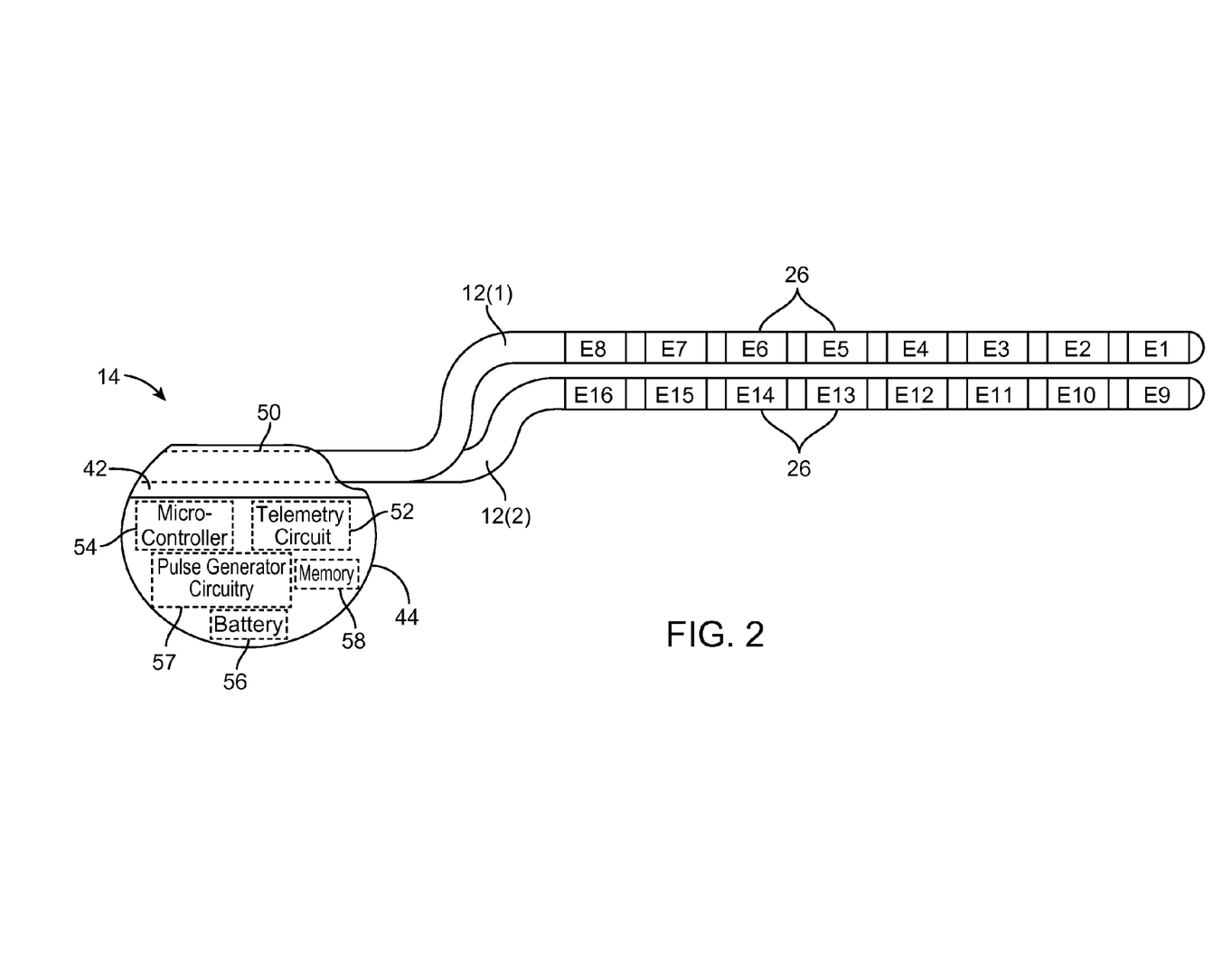
FIG. 2 is a profile view of an implantable pulse generator (IPG) used in the SCM system of FIG. 1.

Referring now to FIG. 2, the external features of the modulation leads 12 and the IPG 14 will be briefly described. One of the modulation leads 12(1) has eight electrodes 26 (labeled E1-E8), and the other modulation lead 12(2) has eight electrodes 26 (labeled E9-E16). The actual number and shape of leads and electrodes will, of course, vary according to the intended application. The IPG 14 includes an outer case 44 for housing the electronic and other components (described in further detail below). The outer case 44 is composed of an electrically conductive, biocompatible material, such as titanium, and forms a hermetically sealed compartment, wherein the internal electronics are protected from the body tissue and fluids. In some cases, the outer case 44 may serve as an electrode. The IPG 14 further comprises a connector 42 to which the proximal ends of the modulation leads 12 mate in a manner that electrically couples the electrodes 26 to the internal electronics (described in further detail below) within the outer case 44. To this end, the connector 42 includes one or more ports 50 for receiving the proximal end(s) of the modulation lead(s) 12. In the case where the lead extensions 24 (shown in FIG. 1) are used, the port(s) 50 may instead receive the proximal ends of such lead extensions 24.

Further, the IPG 14 may include electronic components such as a telemetry circuit 52, a microcontroller 54, a battery 56, memory 58, and other suitable components known to those skilled in the art. The microcontroller 54 executes a suitable program stored in memory 58, for directing and controlling the neuromodulation performed by the IPG 14. Telemetry circuitry 52 (including antenna) is configured for receiving programming data (e.g., the operating program and/or neuromodulation parameters) from the RC 16 in an appropriate modulated carrier signal, and demodulating the carrier signal to recover the programming data, which programming data is then stored in memory 58. The battery 56, which may be a rechargeable lithium-ion or lithium-ion polymer battery, provides operating power to IPG 14.

In addition, the IPG 14 includes pulse generation circuitry 57 that provides electrical conditioning and modulation energy in the form of a pulsed electrical waveform to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode of the array of electrodes 26 (fractionalized electrode configurations), and electrical pulse parameters, which define the pulse amplitude (measured in milliamps or volts depending on whether the IPG 14 supplies constant current or constant voltage to the array of electrodes 26), pulse width (measured in microseconds), pulse rate (measured in pulses per second), and burst rate (measured as the modulation on duration X and modulation off duration Y).

With respect to the pulse patterns provided during operation of the SCM system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case 44, so that the electrical current has a path from the energy source contained within the IPG case 44 to the tissue and a sink path from the tissue to the energy source contained within the case 44. Electrical energy may be transmitted to the tissue in a monopolar or multipolar (e.g., bipolar, tripolar, etc.) fashion. Monopolar delivery occurs when a selected one or more of the lead electrodes 26 is activated along with the case 44 of the IPG 14, so that electrical energy is transmitted between the selected electrode 26 and case 44. Bipolar modulation occurs when two of the lead electrodes 26 are activated as anode and cathode, so that electrical energy is transmitted between the selected electrodes 26. Tripolar delivery occurs when three of the lead electrodes 26 are activated, two as anodes and the remaining one as a cathode, or two as cathodes and the remaining one as an anode.

The electrical energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) modulation pulse and an anodic (positive) recharge pulse that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the recharge pulse). The recharge pulse may be active, in which case, the electrical current is actively conveyed through the electrode via current or voltage sources, or the recharge pulse may be passive, in which case, the electrical current may be passively conveyed through the electrode via redistribution of the charge flowing from coupling capacitances present in the circuit.

Figure 3:
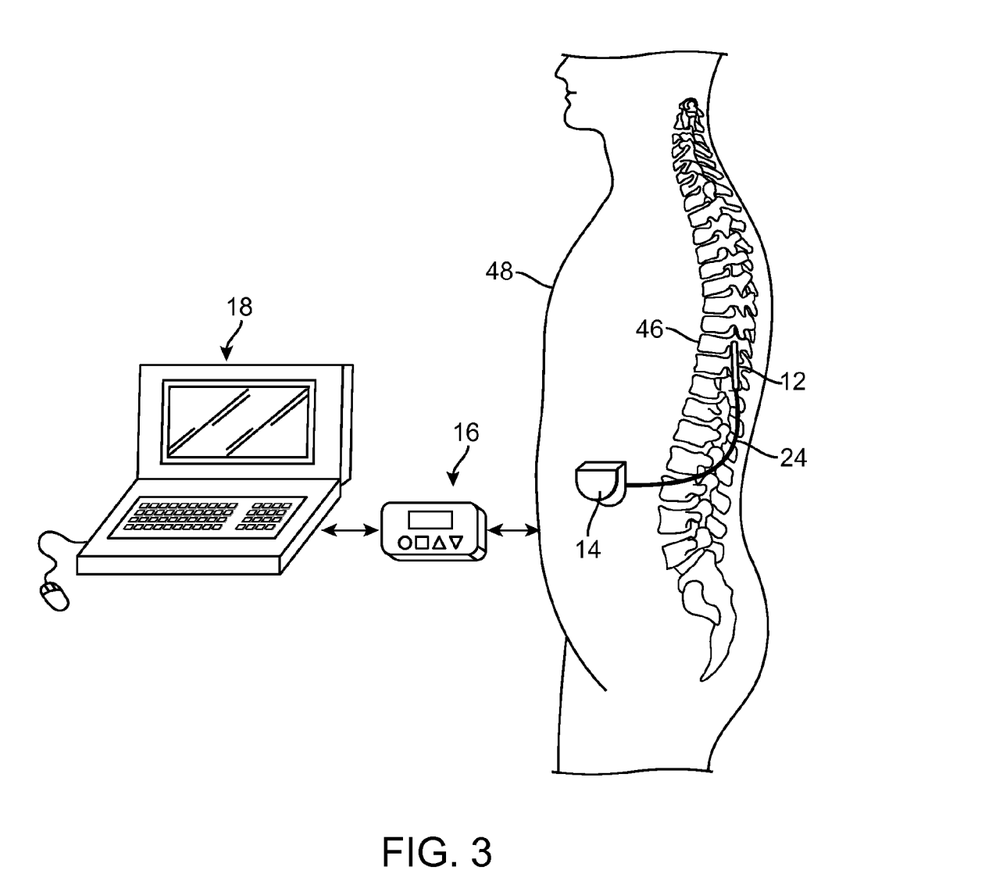
FIG. 3 is a plan view of the SCM system of FIG. 1 in use with a patient.

As shown in FIG. 3, the modulation leads 12 are implanted within the spinal column 46 of a patient 48. The preferred placement of the stimulation leads 12 is adjacent, i.e., resting near, or upon the dura, adjacent to the spinal cord area to be stimulated. Due to the lack of space near the location where the electrode leads 12 exit the spinal column 46, the IPG 14 is generally implanted in a surgically-made pocket either in the abdomen or above the buttocks. The IPG 14 may, of course, also be implanted in other locations of the patient's body. The lead extensions 24 facilitate locating the IPG 14 away from the exit point of the electrode leads 12. As there shown, the CP 18 communicates with the IPG 14 via the RC 16.

Figure 4:
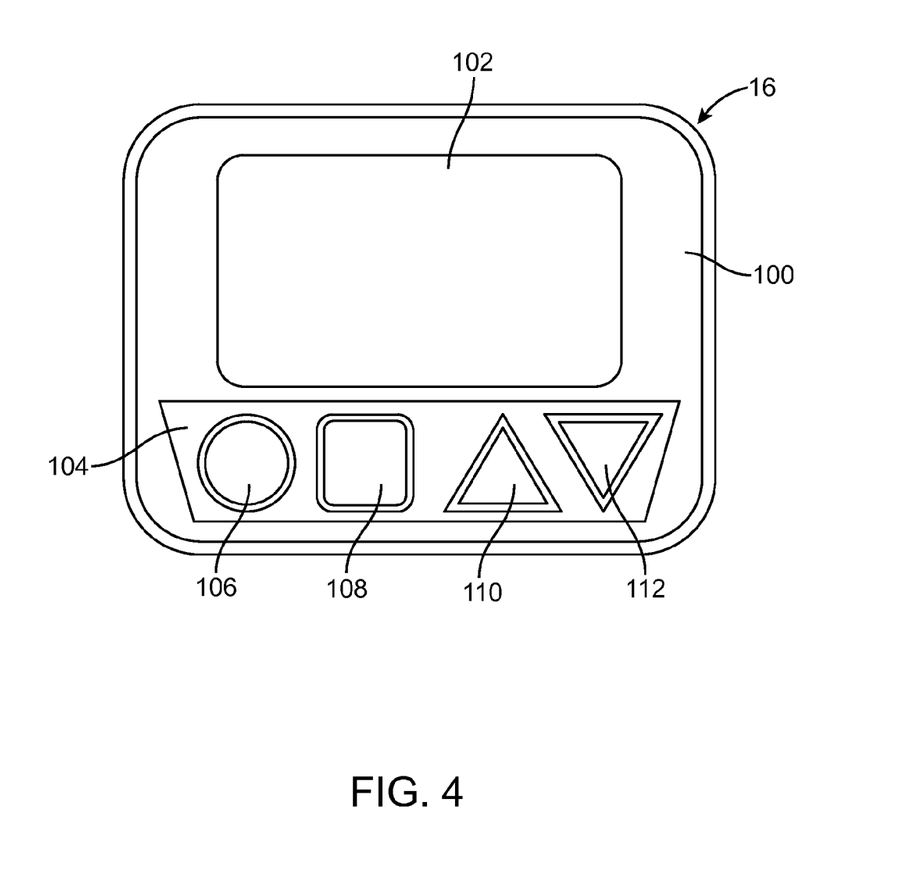
FIG. 4 is a plan view of a hand-held remote control (RC) that can be used in the SCM system of FIG. 1.

Referring now to FIG. 4, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a PCB. In an optional embodiment, the display screen 102 has touchscreen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that allows the RC 16 to switch between screen displays and/or parameters. The buttons 110 and 112 serve as up/down buttons that can be actuated to increase or decrease any of modulation parameters of the pulse generated by the IPG 14, including the pulse amplitude, pulse width, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each stimulation parameter. Rather than using up/down buttons, any other type of actuator, such as a dial, slider bar, or keypad, can be used to increment or decrement the stimulation parameters.

Figure 5:
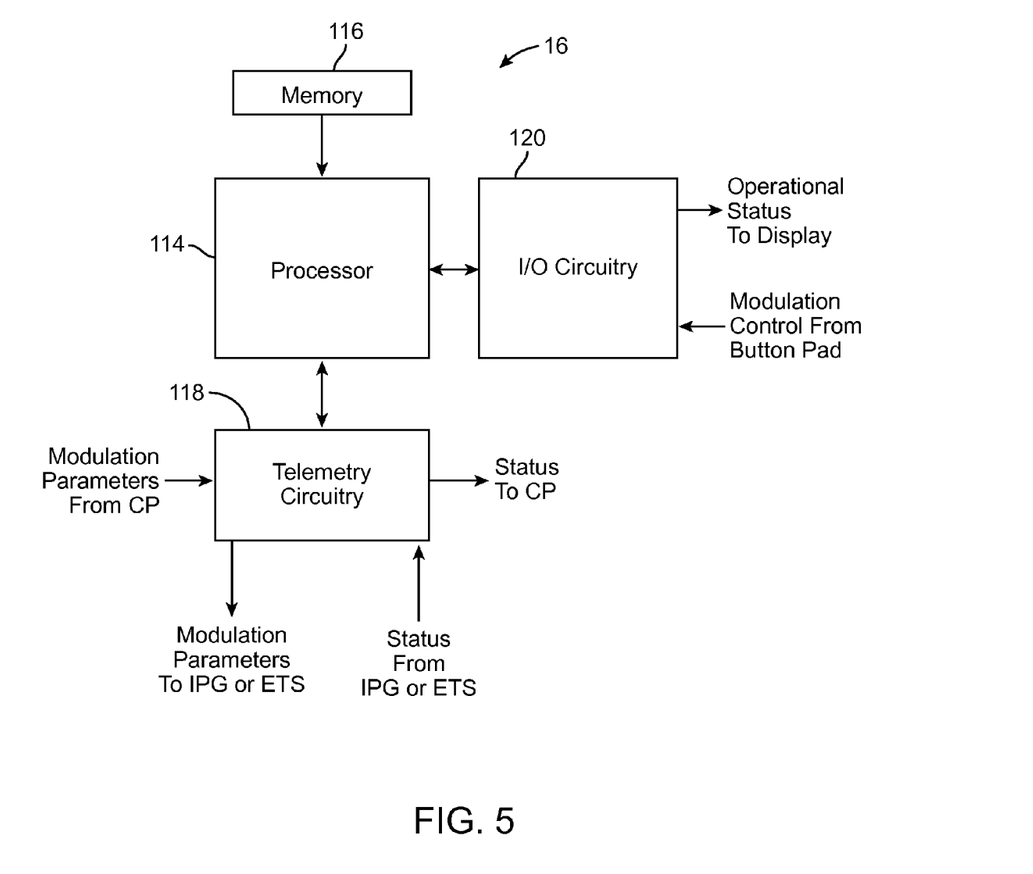
FIG. 5 is a block diagram of the internal components of the RC of FIG. 4.

Referring to FIG. 5, the internal components of an exemplary RC 16 will now be described. The RC 16 generally includes a processor 114 (e.g., a microcontroller), memory 116 that stores an operating program for execution by the processor 114, as well as modulation parameters, telemetry circuitry 118 for outputting modulation parameters to the IPG 14 and receiving status information from the IPG 14, and input/output circuitry 120 for receiving modulation control signals from the button pad 104 and transmitting status information to the display screen 102 (shown in FIG. 4). As well as controlling other functions of the RC 16, which will not be described herein for purposes of brevity, the processor 114 generates a plurality of modulation parameter sets that define the amplitude, phase duration, frequency, and waveform shape in response to the user operation of the button pad 104. These new modulation parameter sets would then be transmitted to the IPG 14 via the telemetry circuitry 118, thereby adjusting the modulation parameters stored in the IPG 14 and/or programming the IPG 14. The telemetry circuitry 118 can also be used to receive modulation parameters from the CP 18. Further details of the functionality and internal componentry of the RC 16 are disclosed in U.S. Pat. No. 6,895,280, which has previously been incorporated herein by reference.

Significantly, the SCM system 10 is configured to adjust the delivered electrical modulation energy in a manner that minimizes the energy consumption required by the IPG 14 to generate the electrical modulation energy while providing efficacious therapy. The SCM system 10 may perform this optimization procedure in response to a user prompt, or may automatically initiate the optimization procedure. In this manner, the electrical modulation energy may be delivered using a modulation parameter that positively impacts battery life and/or recharge interval.

To this end, the SCM system 10 may automatically adjust a modulation parameter value by a step size. In one embodiment, this modulation parameter is a pulse rate, which may be, e.g., 2 Hz-100 KHz. The present invention lends itself well to relatively high frequency pulse rates (e.g., in the range of 1 KHz-50 KHz, and more preferably in the range of 3 KHz-15 KHz), which require a relatively high energy consumption by the IPG 14, and therefore benefit the most by the minimization of the energy consumption. Other types of modulation parameters that can be used are pulse amplitude, pulse width, and pulse duty cycle. In general, the greater the values of the pulse rate, pulse amplitude, pulse width, and pulse duty cycle, the greater the energy consumption required to generate the electrical energy in accordance with these modulation parameter values.

Another type of modulation parameter is the electrode combination. Notably, the spacing between the cathode(s) and anode(s) used to deliver the electrical energy may dictate the energy consumption required to generate the electrical energy. For example, if the spacing between the cathode(s) and anode(s) is relatively small, there may be substantial shunting of electrical current between the cathode(s) and anode(s), thereby requiring a higher energy consumption in the IPG 14. In contrast, if the spacing between the cathode(s) and anode(s) is relatively great, there may be insubstantial shunting of electrical current between the cathode(s) and anode(s), thereby requiring a lower energy consumption in the IPG 14. Thus, the greater the spacing between the cathode(s) and anode(s), the lesser the energy consumption required to generate the electrical energy in accordance with this modulation parameter value.

The step size by which the modulation parameter value is adjusted may depend on the nature of the modulation parameter value, as well as the accuracy of the desired resolution of the energy consumption minimization/processing time. For example, if the stimulation parameter is a pulse rate, the step size may be 1000 Hz, although the step size may be decreased to, e.g., 500 Hz, if more accuracy in the resolution of the energy consumption minimization is desired, or may be increased to, e.g., 2000 Hz if a quicker processing time is desired. As another example, if the stimulation parameter is a pulse amplitude, the step size may be 0.1 mA. If the stimulation parameter is a pulse width, the step size may be 10 µs. If the stimulation parameter is a pulse duty cycle, the step size may be 10%. If the stimulation parameter is an electrode combination, the step size may be the electrode spacing of the modulation lead, e.g., 5 mm.

The SCM system 10 may instruct the IPG 14 to output the electrical energy to electrodes 26 in accordance with the adjusted modulation parameter value. The steps of adjusting the modulation parameter value and applying electrical energy may be repeated until it is determined that the electrical energy applied in accordance with the adjusted modulation parameter value is not effective. This determination is based on whether the modulation parameter set remains stable over a period of time. If the modulation parameter set remains stable over a significant period of time, it can be assumed that the therapy in accordance with the adjusted modulation parameter value remains effective. If the modulation parameter set does not remain stable over a significant period of time (i.e., if the patient manually adjusts the modulation parameter set), it can be assumed that the therapy in accordance with the adjusted modulation parameter value is ineffective. If the electrical energy applied is ineffective, the patient will manually adjust the stimulation energy via the control buttons 110, 112 on the RC 16 (shown in FIG. 4).

If the patient does not make any manual adjustments to any of the modulation parameter values of the stimulation within a predetermined period of time, then the stimulation in accordance with the adjusted modulation parameter value is presumably still efficacious. The predetermined time period may be pre-programmed into the system, or may be set by the clinician. The predetermined period of time may be on the order of minutes, hours, days, etc. For example, the predetermined time period may be less than one minute, less than one hour, less than one day, less than one week, etc.

After the pre-determined time period has passed without the user making a manual adjustment to any one of the parameters of the stimulation, then the adjusted modulation parameter value may be stored in memory (e.g., the memory 58 of the IPG 14 or the memory 116 of the RC 16), or may be deemed a "previously adjusted modulation parameter value" to which the SCM system 10 can revert back. The SCM system 10 repeats the foregoing steps to determine the optimum modulation parameter value that minimizes energy consumption of the IPG 14 when delivering the electrical energy to the electrodes 26.

However, if the patient does make a manual adjustment to one of the modulation parameters, then the electrical energy applied in accordance with the adjusted modulation parameter value is presumably ineffective and the optimization procedure is stopped. Then the SCM system 10 determines that the modulation parameter value that was previously used to provide efficacious therapy (e.g., the "previously adjusted modulation parameter value") is the optimized modulation parameter value. The manual adjustment may include an adjustment to the pulse rate, pulse amplitude, pulse width, pulse duty cycle, and/or the electrode combination. The modulation parameter value adjusted manually by the patient may or may not be the same as the modulation parameter value adjusted automatically by the SCM system 10. For example, if the modulation parameter value adjusted automatically by the SCM system 10 is the pulse rate, the optimization procedure is terminated whether the patient manually adjusts the pulse rate or some other modulation parameter value (e.g., pulse amplitude, pulse width, pulse duty cycle, and/or electrode combination).

Either or both of the memory that stores the adjusted modulation parameter value, and the controller/processor that performs the functions described above, can be contained either in the IPG 14 or the RC 16, or even the CP 18.

The IPG 14 by itself, or the RC 16 may periodically initiate the energy consumption minimization process without user intervention.

Figure 6:
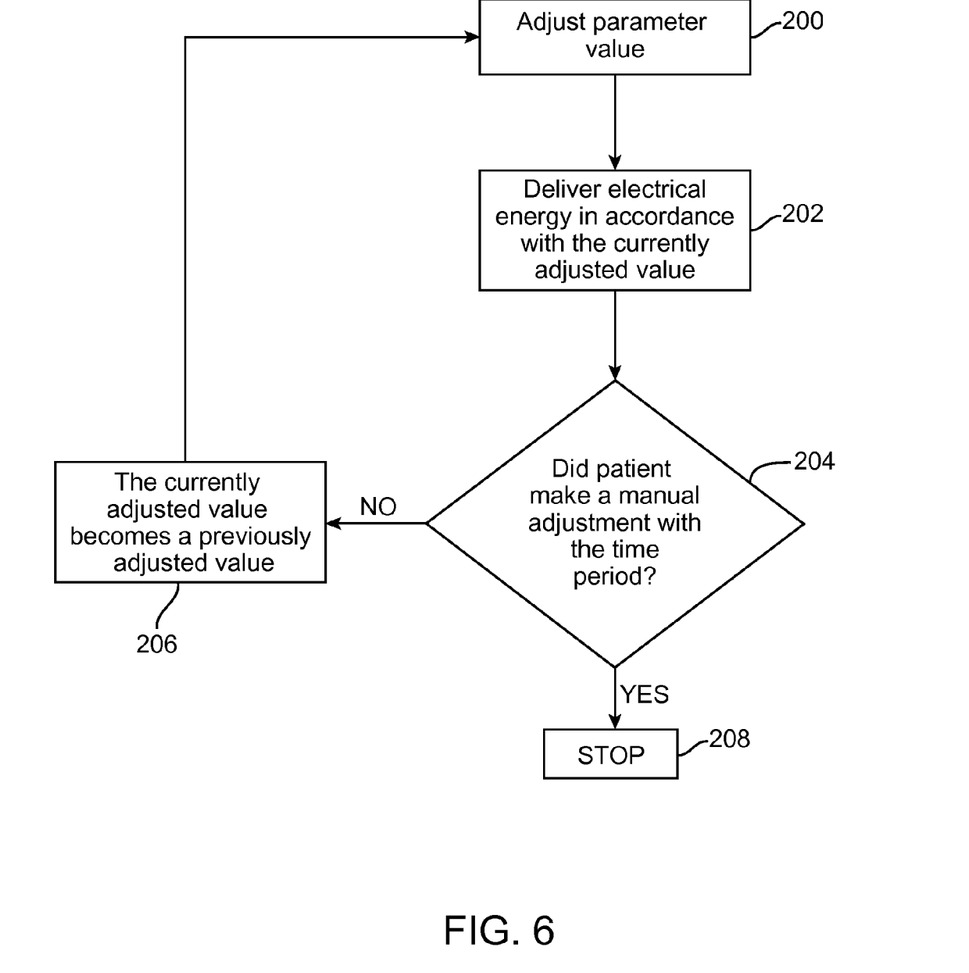
FIG. 6 is a flow diagram illustrating a technique used by the SCM system to minimize the energy consumption in the IPG of FIG. 2.

Having described the structure and function of the SCM system 10, a technique for operating the system 10 to minimize the energy consumption of the IPG 14 while providing efficacious therapy will now be described with reference to FIG. 6. This technique assumes that efficacious therapy is already being provided when electrical energy is delivered from the IPG 14 to the electrodes 26 in accordance with a modulation parameter value.

First, the modulation parameter value is adjusted by a step size, and in particular, adjusted in a manner that decreases the energy consumption of the IPG 14 (step 200). The modulation parameter value adjusted in step 200 may be called the "currently adjusted modulation parameter value." Then, electrical energy is delivered from the IPG 14 to the electrodes 26 in accordance with the currently adjusted modulation parameter value, thereby modulating a target tissue site (step 202). Next, a manual adjustment determination is made (step 204). That is, step 204 includes determining whether the patient made a manual adjustment to one of the modulation parameters within a predetermined time period.

If the patient did not make a manual adjustment, then the currently adjusted modulation parameter value is presumably efficacious, and may be saved or stored. That is, if the patient did not make a manual adjustment, then the currently adjusted modulation parameter value is deemed a "previously adjusted modulation parameter value" (step 206). Next, steps 200, 202, and 204 are repeated to further minimize the energy consumption of the IPG 14.

If the patient did make a manual adjustment to any one of the modulation parameters, then the currently adjusted modulation parameter value is presumably not efficacious, and the method is terminated in step 208. When the method is terminated, the previously adjusted parameter value from step 206 is the optimized modulation parameter value. If step 206 is never performed (i.e., if the user performs a manual adjustment the first time the modulation parameter is adjusted), then the optimized modulation parameter value is the original, un-adjusted, modulation parameter value.

The above technique may be repeated for each modulation parameter value. For example, after determining an optimized pulse rate value, the technique may be repeated to determine an optimized pulse amplitude, an optimized pulse width, an optimized pulse duty cycle, and/or an optimized electrode combination.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An electrical neuromodulation system, comprising:
an external control device configured for receiving input from a user;
a neuromodulation device configured for communicating with the external control device, and configured for delivering electrical energy to at least one electrode in accordance with a modulation parameter value; and
control/processing circuitry configured for automatically performing a process to optimize power consumption that includes (a) adjusting the modulation parameter value to create a currently adjusted modulation parameter value to decrease energy consumption of the neuromodulation device, (b) instructing the neuromodulation device to deliver the electrical energy to the at least one electrode in accordance with the currently adjusted modulation parameter value, (c) determining whether a manual parameter adjustment was made by the user in response to step (b), and (d) repeating steps (a)-(c) until it is determined that the manual parameter adjustment was made by the user in response to step (b), and then determining that a previously-adjusted parameter value is an optimized modulation parameter value that minimizes the energy consumption of the neuromodulation device when delivering the electrical energy to the at least one electrode.

2. The electrical neuromodulation system of claim 1, further comprising memory configured for storing the modulation parameter value.

3. The electrical neuromodulation system of claim 1, wherein the manual parameter adjustment made by the user comprises a manual adjustment of at least one of pulse rate, pulse width, duty cycle, amplitude, or electrode combination.

4. The electrical neuromodulation system of claim 1, wherein the control/processing circuitry is further configured for determining whether the manual parameter adjustment was made within a predetermined time period of step (b) is initiated, and for repeating steps (a)-(c) until it is determined that the manual parameter adjustment was made within the predetermined time period after step (b) is initiated.

5. The electrical neuromodulation system of claim 1, wherein the control/processing circuitry is further configured for, after determining that the manual parameter adjustment was made, automatically instructing the neuromodulation device to again deliver the electrical energy to the at least one electrode in accordance with the previously adjusted modulation parameter value.

6. The electrical neuromodulation system of claim 1, wherein the modulation parameter value is a first modulation parameter value, and wherein the control/processing circuitry is further configured for repeating the steps (a)-(c) by performing a process that includes adjusting a second modulation parameter value to create a currently adjusted second modulation parameter value that decreases the energy consumption of the neuromodulation device, instructing the neuromodulation device to deliver the electrical energy to the at least one electrode in accordance with the currently adjusted second modulation parameter value, determining whether a manual parameter adjustment was made by the user in response to delivery of the electrical energy to the at least one electrode in accordance with the currently adjusted second modulation parameter value.

7. The electrical neuromodulation system of claim 1, wherein the electrical energy is pulsed electrical energy.

8. The electrical neuromodulation system of claim 7, wherein the modulation parameter value is a pulse rate value.

9. The electrical neuromodulation system of claim 7, wherein the modulation parameter value is a pulse width value.

10. The electrical neuromodulation system of claim 1, wherein the modulation parameter value is a duty cycle value.

11. The electrical neuromodulation system of claim 1, wherein the modulation parameter value is an amplitude value.

12. The electrical neuromodulation system of claim 1, wherein the modulation parameter value is an electrode combination value.

13. The electrical neuromodulation system of claim 1, wherein the neuromodulation device is configured for conveying the electrical energy at a frequency in the range of 1 KHz-50 KHz.

14. The electrical neuromodulation system of claim 1, wherein the control/processing circuitry is contained in the neuromodulation device.

15. The electrical neuromodulation system of claim 1, wherein the control/processing circuitry is contained in the external control device.

16. The electrical neuromodulation system of claim 1, further comprising a battery configured for storing power used to generate the electrical energy.

17. The electrical neuromodulation system of claim 1, wherein the control/processing circuitry is configured for automatically adjusting the modulation parameter value by a step size.

18. A method of minimizing energy consumption of a neuromodulation device, the method comprising automatically:
(a) adjusting a modulation parameter value to create a currently adjusted modulation parameter value to decrease the energy consumption of the neuromodulation device;
(b) delivering electrical energy from the neuromodulation device to at least one electrode adjacent a target tissue site in accordance with the currently adjusted modulation parameter value, thereby modulating the target tissue site;
(c) determining whether a manual parameter adjustment was made by a user in response to step (b); and
(d) repeating steps (a)-(c) until it is determined that the manual parameter adjustment was made by the user in response to step (b), and then determining that a previously-adjusted parameter value is an optimized modulation parameter value that minimizes the energy consumption of the neuromodulation device when delivering the electrical energy to the at least one electrode.

19. The method of claim 18, further comprising, after determining that the manual parameter adjustment was made, in delivering the electrical energy to the at least one electrode in accordance with the previously adjusted modulation parameter value.

20. The method of claim 18, wherein the determining whether the manual parameter adjustment was made includes determining whether the manual parameter adjustment was made within a predetermined time period of step (b) is initiated, and the repeating steps (a)-(c) includes repeating steps (a)-(c) until it is determined that the manual parameter adjustment was made within the predetermined time period after step (b) is initiated.

21. The method of claim 18, wherein the modulation parameter value is a firm modulation parameter value. and the repeating the steps (a)-(c) includes performing a process that includes:
adjusting a second modulation parameter value to create a currently adjusted second modulation parameter value that decreases the energy consumption of the neuromodulation device;
delivering the electrical energy from the neuromodulation device to the at least one electrode adjacent the target tissue site in accordance with the currently adjusted second modulation parameter value, thereby modulating the target tissue site;
determining whether the manual parameter adjustment was made by a user in response to the delivering the electrical energy in accordance with the currently adjusted second modulation parameter.

22. The method of claim 18, wherein the manual parameter that is adjusted includes at least one of pulse rate, pulse width, duty cycle, amplitude, or electrode combination.

23. The method of claim 18, wherein the electrical energy is pulsed electrical energy.

24. The method of claim 23, wherein the modulation parameter value is a pulse rate value.

25. The method of claim 23, wherein the modulation parameter value is a pulse width value.

26. The method of claim 18, wherein the modulation parameter value is a duty cycle value.

27. The method of claim 18, wherein the modulation parameter value is an amplitude value.

28. The method of claim 18, wherein the modulation parameter value is an electrode combination value.

29. The method of claim 18, wherein the electrical energy is delivered from the neuromodulation device at a frequency in the range of 1 KHz-50 KHz.

30. The method of claim 18, wherein the at least one electrode is implanted within the patient.

31. The method of claim 18, wherein the delivery of the electrical energy from the neuromodulation device to the at least one electrode stimulates the target tissue site.

32. The method of claim 18, wherein the modulation parameter value is adjusted by a step size.

33. An electrical neuromodulation system, comprising:
an external control device configured to receive input from a user;
a neuromodulation device configured to communicate with the external control device and to deliver electrical energy to at least one electrode in accordance with a modulation parameter value; and
control/processing circuitry configured to automatically perform a process to optimize power consumption for the neuromodulation device that includes:
adjusting the modulation parameter value to create a currently adjusted modulation parameter value to decrease the energy consumption of the neuromodulation device, and instructing the neuromodulation device to deliver the electrical energy to the at least one electrode in accordance with the currently adjusted modulation parameter value, and then determining whether a manual parameter adjustment was made by the user in response to delivery of the electrical energy to the at least one electrode in accordance with the currently adjusted parameter value; and
repeating the adjusting, the instructing and the determining until it is determined that the manual parameter adjustment was made by the user, and then determining that the previously-adjusted parameter value is an optimized modulation parameter value that minimizes energy consumption of the neuromodulation device when delivering the electrical energy to the at least one electrode.

34. The electrical neuromodulation system of claim 33, wherein the control/processing circuitry is further configured to adjust at least one modulation parameter selected from the group of parameters consisting of pulse rate, pulse width, duty cycle, amplitude, and electrode combination during the automatically-performed process to optimize power consumption.

\* \* \* \* \*